United States Patent [19]

Lance

[11] Patent Number: 5,248,700

[45] Date of Patent: Sep. 28, 1993

[54] ACTIVE AGENT CONTAINING SOLID STRUCTURES FOR PROLONGED RELEASE OF ACTIVE AGENTS

[75] Inventor: Wolfgang Lance, Obernburg, Fed. Rep. of Germany

[73] Assignee: AKZO NV, Arnheim, Netherlands

[21] Appl. No.: 341,929

[22] Filed: Apr. 21, 1989

Related U.S. Application Data

[63] Continuation of Ser. No. 496,293, May 16, 1988, abandoned.

[30] Foreign Application Priority Data

May 14, 1982 [DE] Fed. Rep. of Germany ....... 3218150

[51] Int. Cl.$^5$ .............................................. A61K 47/32
[52] U.S. Cl. .................................. 514/772.3; 424/426; 424/428; 424/469; 424/470
[58] Field of Search .................. 424/78, 426, 428, 469, 424/470; 514/772.3

[56] References Cited

U.S. PATENT DOCUMENTS

| | | | |
|---|---|---|---|
| 3,755,558 | 8/1973 | Scribner et al. | 424/78 |
| 3,773,919 | 11/1975 | Boswell et al. | 424/78 |
| 3,923,969 | 12/1975 | Bankal et al. | 424/357 |
| 3,989,649 | 11/1976 | Kaiho et al. | 521/146 |
| 4,014,335 | 3/1977 | Arnold | 424/427 |
| 4,110,529 | 8/1978 | Story | 528/491 |
| 4,122,129 | 10/1978 | Easey et al. | 424/78 |
| 4,138,344 | 2/1979 | Choi et al. | 424/426 |
| 4,322,311 | 3/1982 | Lim et al. | 252/316 |
| 4,439,178 | 3/1984 | Brightman, II et al. | 424/426 |
| 4,522,953 | 6/1985 | Barby et al. | 521/64 |

FOREIGN PATENT DOCUMENTS

| | | |
|---|---|---|
| 0163178 | 4/1985 | European Pat. Off. . |
| 2424169 | 12/1974 | Fed. Rep. of Germany ...... 424/426 |
| 3218150 | 9/1986 | Netherlands . |

*Primary Examiner*—Peter F. Kulkosky
*Attorney, Agent, or Firm*—Michael J. Striker

[57] ABSTRACT

A solid mixture of a degradable polymer (B) in which an active agent loaded microporous powder or granulate form polymer (A) is uniformly dispersed. The active agent loaded polymer (A) is distributed throughout said polymer matrix by simple stirring of polymer (A) in a melt of polymer (B) or through kneading of polymer (A) and (B) or through coextrusion of polymers (A) and (B). The preparation of powder or granulate form structures and of shaped solid structures is possible according to the invention. The speed of degradation of polymer (B) in the selected surrounding environment, for instance, a human or animal body, determines the release rate of the active agent so that the release takes place in accordance with a velocity rule zero arrangement and is a constant or invariable. In this manner the release of the active agent into the surrounding environment or mileau is controlled and maintained according to predetermined conditions. The solid structures of the invention are suitable for the release of solid and liquid active agents such as medicaments, hormones, fertilizers, pesiticides and the like. Preferably, the polymers used are based on polylactides.

7 Claims, No Drawings

ACTIVE AGENT CONTAINING SOLID STRUCTURES FOR PROLONGED RELEASE OF ACTIVE AGENTS

This is a continuation of application Ser. No. 496 293, filed May 16, 1983, now abandoned.

BACKGROUND OF THE INVENTION

This invention relates to solid structures containing active agents such as pharmaceuticals, pesticides, peptides, hormones, enzymes and the like which are adapted for the controlled and prolonged release of the active agent into the surrounding environment. More particularly the invention relates to such solid structures adapted for controllably releasing the active agent(s) contained therein over a prolonged period of time.

The invention further relates to a process for preparing such active agent containing solid structures and as well to a method for providing prolonged release of active agents under controlled conditions of time and concentration.

Numerous attempts have been made to control the mechanism of the release of active agents such as medicaments, hormones, fertilizers, pesticides, trace elements, fragrances and the like so that their release is prolonged i.e., their release takes place over a prolonged period of time.

In the pharmaceutical applications of prolonged release drug forms, the active agent until now has almost always been administered orally in the form of tablets or pills, as liquid solutions or dispersions to be taken orally and as injection solutions or dispersions. In these forms, the medicament is fairly quickly made available in a high concentration. The concentration is over the course of time decreased. The uptake of the active agent which takes place almost always follows an exponential path. From this, it can be easily appreciated that this type of dispensing of active agent provides a thereapeutically significant concentration level for only a short period of time.

Further initially there can be provided a too high drug dosage level so that there exists the danger of an overdose. Later as time passes and the concentration of drug level decreases, there may be insufficient drug available for effective thereapeutic results to be realized.

It can be appreciated that, for most purposes, it is desirable to provide a constant level of active agent and this over a prolonged period.

The same is true in agricultural and forestry fields of application. Fertilizers are mostly used in the form of powders, for example ammonium phosphate powder, and in this form distributed over the planting field, whereby at first a high fertilizer concentration is established. With the first rain, a considerable amount of the salt is washed away or seeps away so that the concentration in the ground is decreased and less of the active agent is available for the plants.

Attempts have been made in order to overcome these previously mentioned disadvantages. For example, the active agent has been introduced in a microporous powder permitting the active agent to be released over a longer period of time.

Also, and particularly in pharmaceutical applications, so-called microcapsules have been employed wherein the active agent is enclosed within a membrane through which it is then diffused. The disadvantage attendant the use of microcapsules lies in that selecting and achieving a desired thickness of the separating partition and required wall strength for obtaining the aimed-for release rate is very difficult. Often the capsules are not totally impervious, or are not strong enough so that when any stress is applied, uncontrolled release of active agent can take place.

It has also been proposed to dispense the active agent in a matrix from which the active agent through diffusion can be discharged into the surrounding environment. The disadvantage of this approach is that the release of the active agent takes place in a graduated fashion and is not possible to arrive at a constant release to be delivered over a prolonged period of time.

In U.S. Pat. Nos. 3,887,699 and 4,011,312 there are described similar or analogous methods for achieving prolonged release of active agents. The patents describe methods of dispensing an active agent in a polymeric material, so that the active material will be diffused from the surface layer of the polymer.

The disadvantage of the described process is that the active agent can only be dispersed in the polymer matrix in limited amounts and in order to insure its retention in the matrix its handling and working is difficult. Despite observed precautions, the active agent, before actual use of the active agent treated matrix already to a considerable extent has separated out of the polymer.

There, therefore still exists a need for improved units which contain at least one active agent which can be released into the environment in a controlled manner over a prolonged period of time.

SUMMARY OF THE INVENTION

An object of this invention is to provide a process which is simple and economically feasible and which can be used for preparing these solid structures or units for prolonged release of active agents.

A further object of this invention is to provide polymers for loading with the active agent and further polymers which can serve as the matrix for the loaded polymers, at least the matrix polymers being degradable.

Still a further object of the invention is to make available active agent/polymer systems in which the active agent can be introduced in broadly varying amounts so that the intensity of the constantly released active agent is satisfactorily and reproducibly established.

Another object of the invention is to make available polymer/active agent systems that are versatile and can be introduced into physiological systems in which biocompatible polymers are suitable.

Yet another object of the invention is to make available a polymer/active agent system in which constant release rates are assured and in which the release takes place in accordance with a velocity rule zero arrangement.

Still another object of the invention is to make available a polymer/active agent system which can be charged with different active agents in different concentrations.

These and other objects and advantages are realized in accordance with the invention through a process for preparing an active agent containing solid structure or unit adapted for prolonged release of such active agent comprising loading a powder or granulate form microporous polymer (A) with active agent and distributing this active agent containing polymer in a matrix of degradable polymer (B). Preferably the distribution of the microporous active agent containing polymer (A) is carried out in a melt of the degradable polymer (B). The melting point of said polymer (B) should lie below that of the microporous polymer (A). The melt thus formed is then cooled. For use as degradable polymer (B) there are especially suitable polymers which are biodegradable in the human or animal body. For the aforesaid purpose, all of the degradable polymers of lactic acid may be used. It has been found especially advantageous to use as microporous polymer (A) a similarly degradable polymer. Particularly favorable results are realized if the microporous polymer (A) has a degradation velocity which is lower than the degradation velocity of the matrix polymer (B).

In accordance with another embodiment of the invention, the polymer (B) is a plasticized polymer. For this purpose, the conventional plasticizers can be used. It is, of course, understood that for the aforesaid objectives to be realized the plasticizer selected for use in the active agent containing units must be compatible with the ultimate intended use of the units. Thus, it is necessary, if the active agent containing release units are going to be used in humans or animals, that no toxic or injurious plasticizers be used. When the polymer (B) is a plasticizer polymer, it is still necessary that its melting point is lower than the melting point of the polymer (A).

The distibution of the active agent loaded polymer (A) in polymer (B) can, for example, take place through simple stirring in a melt of (B) or through kneading of (A) and (B) together, or through coextrusion.

In accordance with the invention, the active agent containing unit adapted for the prolonged release of active agent is characterized by a matrix of degradable polymer (B) in which the active agent charged microporous powder or granulate polymer (A) is uniformly distributed.

Preferably as the polymer (A) there is selected a likewise or similarly degradable polymer whose degradation velocity is less than the degradation velocity of the matrix polymer (B). Most preferably the degradable polymer (B) is a copolymer of lactic acid.

An especial advantage of the invention is the possibility of using solid as well as liquid active agents in amounts not heretofore attainable and that the same can be introduced into the polymer (A) and therewith into the system for storage therein and from which over prolonged periods of time amounting to many months and extending up to one-half year and more they can be released in a controlled manner. A further advantageous aspect of the invention is that it allows with only one unit to provide a multiplicity of active agents whose relative concentrations taken singly and one to the other can be predetermined and then in such controlled relationships be delivered into the environment. The conventional combinations of active agents known in the pharmaceutical arts and other arts as for instance, agriculture, forestry, etc. can be used and then these agents, separately or already in the form of their mixtures, introduced into the microporous powdery polymer (A) in the desired amounts and relationships. The loaded microporous polymeric material is then distributed in the matrix polymer (B). The active agents can be selected from the following groups: medicinal agents, hormones, vitamins, anti-microbial agents, fertilizers, pesticides, plant growth regulating agents and fragrances.

As polymeric microporous material contemplated as coming within the scope of the invention, there come particularly to mind, polylactides on the basis of dl−lactic acid, polymers of l(+)−lactic acid, of d(−)−lactic acid and copolymers thereof as aforementioned.

Further, it is possible to polymerize one or more of the named lactic acids with other monomers such as for example glycolide, caprolactam, B-propiolactone, etc.

The following Example is given in order to more fully illustrate the invention but is not to be taken as limitative of the scope thereof.

EXAMPLE

A cylindrical release unit having a length of 20 mm and a diameter of 2 mm and having a planned life span of about 6 months was prepared by in a first step preparing a copolymer consisting of 75% (weight) L(+)−lactide and 25% glycolide through block polymerization with 0.03 wt. % zinc octoate and 0.01 wt. % lauryl alcohol as catalyst (Polymer 1979, Vol. 20, p. 1459).

This was accomplished by heating together 7.5 g L(+)−dilactide with 2.5 g glycolide (prepared according to Polymer 1979, Vol. 20, p. 1459) for 2 hours at a temperature of 200° C. in a bomb tube. Following completion of the reaction, the contents of the bomb tube were allowed to cool and the bomb tube then opened. The contents which were in the form of a melt were poured out. The melting point of the copolymer was determined and gave a value of 58° C. which corresponded with the value reported in the literature (Polymer 1979, Vol. 20, P. 1463).

There was next prepared the carrier for the active agent, i.e., the microporous polylactide polymer. This was accomplished by dissolving 90.3 g d(−)−polylactide having a molecular weight of about 40,000 in 400 ml xylene and then without any stirring, the solution allowed to cool. The, thereby obtained homogeneous separated mass was filtered-off and vacuum dried at 60° C. Hg intrusion measurement of the dry powder gave a value of 55% for the pore volume.

10 g of the microporous polylactide was treated with 100 ml 50% ethanolic solution of cetyl alcohol as test substance at room temperature and under vacuum. The excess lquid was carefully removed with suction filtering and the alcohol moist powder dried under vacuum at room temperature. Gravimetric analysis of the dried powder gave a value for loading of the powder of about 58%.

The release structure according to the invention was prepared by kneading 10 g of the cetyl alcohol loaded polylactide powder together with 19 g of the dilactide-glycolide copolymer at about 55° C. until the mass was entirely homogeneous. This latter product was extruded at about 55° C. using a laboratory extrusion meter provide with a nozzle having a diameter of about 2 mm.

The solid structure or unit thus formed had a cetyl alcohol loading of 20% calculated on the total weight of the unit.

We claim:

1. An active agent containing solid structure adapted for prolonged release of said active agent, said active agent containing solid structure comprising a matrix of a degradable polymer (B) and a microporous powder form polymer (A) loaded with said active agent, said microporous powder form polymer (A) being uniformly distributed in said matrix.

2. An active agent containing solid structure according to claim 1, wherein said polymer (A) is also degradable.

3. An active agent containing solid structure according to claim 2 wherein the degradation velocity of said polymer (A) is less than the degradation velocity of said matrix polymer (B).

4. An active agent containing solid structure according to claim 2 wherein as said degradable polymer (B) a copolymer of lactic acid is used.

5. An active agent containing solid structure according to claim 1, wherein the microporous powder form polymer (A) is loaded with other active agents different from said active agent.

6. An active agent containing solid structure according to claim 1, wherein said active agent is selected from the group consisting of medicinal agents, hormones, enzymes, vitamins, anti-microbial agents, fertilizers, pesticides, plant growth regulating agents and fragrances.

7. Method of controllably dispensing an active agent at a predetermined location so as to provide a prolonged release of the active agent, said method comprising introducing an active agent containing solid structure according to claim 1 which contains the active agent into the predetermined location.

* * * * *

UNITED STATES PATENT AND TRADEMARK OFFICE
CERTIFICATE OF CORRECTION

PATENT NO. : 5,248,700

DATED : September 28, 1993

INVENTOR(S) : Wolfgang LANGE

It is certified that error appears in the above-identified patent and that said Letters Patent is hereby corrected as shown below:

On title page, item [19], "Lance" should read --Lange--

On title page, item

[75] the name of the inventor should read --Wolfgang Lange--

Signed and Sealed this

Twenty-second Day of March, 1994

Attest:

BRUCE LEHMAN

Attesting Officer　　　Commissioner of Patents and Trademarks